United States Patent [19]

Fukaya et al.

[11] Patent Number: 4,983,584
[45] Date of Patent: Jan. 8, 1991

[54] THERAPEUTIC AND PROPHYLACTIC AGENTS FOR PEPTIC ULCERS

[75] Inventors: Chikara Fukaya; Hitoshi Yasuda; Toshiaki Akira; Masakazu Iwai; Kanemichi Okano; Kazumasa Yokoyama, all of Osaka, Japan

[73] Assignee: Green Cross Corporation, Osaka, Japan

[21] Appl. No.: 124,139

[22] Filed: Nov. 23, 1987

[30] Foreign Application Priority Data

Nov. 22, 1986 [JP] Japan .................. 61-279181
Nov. 22, 1986 [JP] Japan .................. 61-279182
Nov. 22, 1986 [JP] Japan .................. 61-279183

[51] Int. Cl.$^5$ .................. A61K 31/00; C07C 13/00
[52] U.S. Cl. .................. 514/54; 514/25; 514/53; 514/763; 514/927; 585/20; 568/376
[58] Field of Search .................. 514/54, 927, 928, 53, 514/25, 763; 568/376; 585/20

[56] References Cited

U.S. PATENT DOCUMENTS 3,995,055 11/1976 Sentoku et al. .................. 514/551
4,631,292 12/1986 Tomiyama et al. .................. 514/452
4,888,417 12/1989 Shiraga et al. .................. 514/927

OTHER PUBLICATIONS

Morrison and Boyd, Organic Chemistry, Third Edition (1973), Allyn and Bacon, Inc., p. 286.

*Primary Examiner*—Ronald W. Griffin
*Assistant Examiner*—Everett White
*Attorney, Agent, or Firm*—Sughrue, Mion, Zinn, Macpeak & Seas

[57] ABSTRACT

A therapeutic and prophylactic agent for peptic ulcers comprising as an effective ingredient a cyclohexane derivative represented by general formula (I):

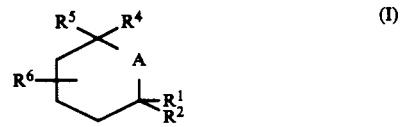

(I)

wherein A represents a group shown by formula, $>CH_2$,

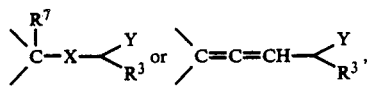

wherein X represents ethynylene, vinylene or ethylene, Y represents oxo or a hydroxy group; $R^1$, $R^3$, $R^4$ and $R^5$ each represents a hydrogen atom or alkyl; $R^2$ represents a hydrogen atom, alkyl or a group shown by $-OR^8$;

$R^6$ represents a hydrogen atom, oxo or a group shown by $-OR^8$; and $R^7$ represents a hydrogen atom or a group shown by $-OR^8$, wherein $R^8$ represents a hydrogen atom or an organic residue.

8 Claims, No Drawings

THERAPEUTIC AND PROPHYLACTIC AGENTS FOR PEPTIC ULCERS

FIELD OF THE INVENTION

The present invention relates to therapeutic and prophylactic agents for peptic ulcers comprising cyclohexane derivatives as effective ingredients.

BACKGROUND OF THE INVENTION

A variety of compounds have been hitherto known as therapeutic and prophylactic agents for peptic ulcers. In recent years, the occurrence of ulcers has tended to increase and development of effective therapeutic and prophylactic agents has thus been an important problem.

SUMMARY OF THE INVENTION

Accordingly, an object of the present invention is to provide novel therapeutic and prophylactic agents for peptic ulcers having excellent anti-ulcer activity.

As a result of extensive investigations to develop therapeutic and prophylactic agents for peptic ulcers, the present inventors have found that compounds represented by general formula (I) described below have excellent anti-ulcer activity and exhibit a therapeutic and prophylactic effect, particularly on ethanol-induced ulcer and serotonin-induced ulcer.

DETAILED DESCRIPTION OF THE INVENTION

Namely, the present invention relates to therapeutic and prophylactic agents for peptic ulcers comprising in an amount effective to therapeutically and/or prophylactically treat peptic ulcer, a cyclohexane derivative (hereinafter referred to as compound (I)) represented by general formula (I):

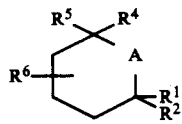
(I)

wherein A represents a group shown by formula, $>CH_2$,

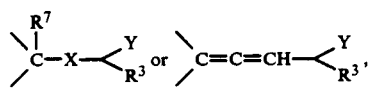

wherein X represents ethynylene, vinylene or ethylene, Y represents oxo or a hydroxy group; $R^1$, $R^3$, $R^4$ and $R^5$ each represents a hydrogen atom or alkyl; $R^2$ represents a hydrogen atom, alkyl or a group shown by $-OR^8$;

$R^6$ represents a hydrogen atom, oxo or a group shown by $-OR^8$; and $R^7$ represents a hydrogen atom or a group shown by $-OR^8$, wherein $R^8$ represents a hydrogen atom or an organic residue.

As the alkyl shown by $R^1$, $R^2$, $R^3$, $R^4$ and $R^5$ in general formula (I), preferred are alkyl groups having from 1 to 6 carbon atoms, more preferably 1 to 4 carbon atoms. These alkyl groups may be straight-chain or branched-chain. Specific examples thereof include methyl, ethyl, n-propyl, iso-propyl, n-butyl, t-butyl, n-pentyl. The alkyl groups may be substituted at an optional position thereof. Examples of the substituent include hetero atoms and an aromatic ring.

The active moiety in the therapeutic and prophylactic agents for peptic ulcers according to the present invention is a moiety represented by formula:

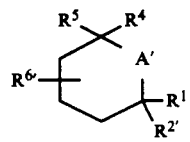

wherein A' represents a group shown by formula $>CH_2$,

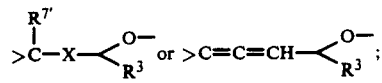

$R^1$, $R^3$, $R^4$, $R^5$, and X have the same meanings as defined above; $R^{2'}$ represents a hydrogen atom, alkyl or $-O-$; and $R^{6'}$ and $R^{7'}$ each represents a hydrogen atom or $-O-$. Accordingly, the organic residues represented by $R^8$ are not particularly limited as long as they are pharmaceutically acceptable. Specific examples of the organic residues include alkyl, acyl, alkoxycarbonyl, alkoxycarbonylalkyl, carboxyalkyl, carboxyalkylcarbonyl, cyclic acetal, and an oligosaccharide residue having from 1 to 3 sugar units.

As the alkyl which is one of the organic residues, groups having from 1 to 6 carbon atoms are preferred, with particular preference of 1 to 4 carbon atoms. These alkyl groups may be straight-chain or branched-chain. Specific examples thereof include methyl, ethyl, n-propyl, iso-propyl, n-butyl, t-butyl, n-pentyl. As the alkoxy moiety in the alkoxycarbonyl, groups having from 1 to 6 carbon atoms are preferred, with particular preference of 1 to 4 carbon atoms. These alkoxy groups may be straight-chain or branched-chain. Specific examples of the alkoxy moiety include methoxy, ethoxy, n-propoxy, iso-propoxy, n-butoxy, t-butoxy. Examples of the alkoxycarbonyl include methoxycarbonyl, ethoxycarbonyl, etc. As the acyl, any of aliphatic and aromatic groups may be used. Examples of the aliphatic acyl are groups having from 1 to 6 carbon atoms, preferably 2 to 5 carbon atoms, such as acetyl, propionyl, butyryl, valeryl, etc. As the aromatic acyl, mention may be made of benzoyl or the like as examples. As the alkoxy moiety in the alkoxycarbonyl, the same groups as described above are exemplified and examples of the alkoxycarbonyl include methoxycarbonyl, ethoxycarbonyl, etc. As the alkoxy moiety and alkyl moiety in the alkoxycarbonyl, the same groups as described above are exemplified and examples of the alkoxycarbonylalkyl include methoxycarbonylmethyl, etc. As the alkyl moiety in the carboxyalkyl, the same groups as described above are exemplified and examples of the carboxyalkyl include carboxymethyl, etc. As the alkyl moiety in the carboxyalkylcarbonyl, the same groups as described above are exemplified and examples of the carboxyalkylcarbonyl include carboxyethylcarbonyl, etc. As the cyclic acetal, tetrahydropyranyl is exemplified. The oligosaccharide residue having from 1 to 3 sugar units refers to mono-, di- or tri-glycoside residues. Their constituent sugar is not particularly limited. Specific examples of the mono-glycoside residue include glucosyl group, arabinosyl group, galactosyl group, mannosyl group, fructosyl group, xylosyl group, ribosyl group, apiosyl group, glucosamine group, etc. Specific examples of the di-glycoside residue include apiosylglucosyl group, succrosyl group, maltosyl group, lactosyl group, gentiobiosyl group, etc. Specific examples of the tri-glycoside residue include apiosylgentiobiosyl group, gentianosyl group, raffinosyl group, etc. The hydroxy groups of these sugar moieties may be substituted in part or wholly with the lower alkyl, acyl, alkoxycarbonyl, alkoxycarbonylalkyl, carboxyalkyl, carboxyalkylcarbonyl or cyclic acetal described above.

The compound (I) is a known compound and can be prepared by the processes described in or similar to, for example, S. Isoe et al., Tet. Lett., 5561 (1968), Japanese Patent Publication No. 44658/83; A. Haag et al., Helv. Chim. Acta., 63, 10 (1980); W. Skorianetz et al., Helv. Chim. Acta., 58, 771 (1975); F. W. Nader et al., Chem. Ber., 118, 4314 (1985); J. Meinvald et al., Tet. Lett., 1657 (1969).

As the compound (I), the following compounds are exemplified:

(a) 1-(2-Hydroxy-2,6,6-trimethylcyclohexylidene)-but-1-en-3-ol (b) 1-(2-Hydroxy-2,6,6-trimethylcyclohexyl)-but-1-en-3-ol (c) 1-(2-Hydroxy-2,6,6-trimethylcyclohexyl)-but-1-yn-3-ol (d) 1,5,5-Trimethyl-1,3-cyclohexandiol (e) 4-(2,4-Dihydroxy-2,6,6-trimethylcyclohexylidene)-but-3-en-2-ol (f) 4-(1,4-Dihydroxy-2,6,6-trimethylcyclohexyl)-but-3-yn-2-ol (g) 4-(1-Hydroxy-4-oxo-2,6,6 trimethylcyclohexyl)-but-3-yn-2-ol Next, methods for experiments performed to confirm pharmacological effects of the compound (I), acute toxic test and mode of administration and the results are shown below.

The compounds used are:

(I-1): 1-(2-Hydroxy-2,6,6-trimethylcyclohexylidene)-but-1-en-3-ol (I-2): 1-(2-Hydroxy-2,6,6-trimethylcyclohexyl)but-1-en-3-ol (I-3): 1-(2-Hydroxy 2,6,6-trimethylcyclohexyl)but-1-yn-3-ol (I-4): 1,5,5-Trimethyl-1,3-cyclohexanediol (I-5): 4-(2,4-Dihydroxy-2,6,6-trimethylcyclohexylidene)-but-3-en-2-ol (I-6): 4-(1,4-Dihydroxy-2,6,6-trimethylcyclohexyl)but-3-yn-2-ol

PHARMACOLOGICAL EFFECTS (1) Serotonin-induced Ulcer

After fasting for a day, Wistar strain male rats (weighing 160 to 180 g) were used for the experiment. Serotonin creatinine sulfate (30 mg/5 ml) were subcutaneously administered on the back of each rat in a dose of 5 ml per 1 kg of body weight. The stomach was excised 6 hours after the administration of serotonin. The total sum of areas of hemorrhagic erosion was measured as an ulcer index. The test compound was given to the rat into the stomach through an oral catheter 30 minutes prior to the administration of serotonin.

(2) Ethanol-induced Ulcer

After fasting for a day, 70% (v/v) of ethanol was administered Wistar strain male rats (weighing 160 to 180 g) into the stomach through an oral catheter in a dose of 1 ml per each rat. The test compound was given to the rat into the stomach through an oral catheter 30 minutes prior to the administration of ethanol. The stomach was excised an hour after the administration of ethanol. The long diameter of hemorrhagic erosion at the glandular stomach was measured and the total sum was made an ulcer index.

The results are shown in the Table below.

TABLE

| Model of Ulcer | Serotonin-Induced Ulcer | | | Ethanol-Induced Ulcer | | |
| --- | --- | --- | --- | --- | --- | --- |
| Dose of Compound (I-1) (inhibitory rate) | 0.02 | μg/kg | (16.4%) | 0.06 | μg/kg | (66.3%)* |
|  | 0.12 | μg/kg | — | 0.6 | μg/kg | (56.2%)* |
|  | 0.72 | μg/kg | (41.6%) | 6 | μg/kg | (53.2%)* |
| Dose of Compound (I-2) (inhibitory rate) |  |  |  | 0.06 | μg/kg | (49.8%)* |
|  |  |  |  | 0.6 | μg/kg | (41.4%)* |
|  |  |  |  | 6 | μg/kg | (42.7%)* |
| Dose of Compound (I-3) (inhibitory rate) |  |  |  | 0.06 | μg/kg | (48.8%) |
|  |  |  |  | 0.6 | μg/kg | (41.4%) |
|  |  |  |  | 6 | μg/kg | (37.6%) |
| Dose of Compound (I-4) (inhibitory rate) | 0.015 | μg/kg | (58.2%) | 0.045 | μg/kg | (14.1%) |
|  | 0.09 | μg/kg | (12.3%) | 0.65 | μg/kg | (11.5%) |
| Dose of Compound (I-5) (inhibitory rate) | 0.02 | μg/kg | (66.5%)* | 0.065 | μg/kg | (63.4%)* |
|  | 0.13 | μg/kg | (41.0%) | 0.65 | μg/kg | (60.0%)* |
|  |  |  |  | 6.5 | μg/kg | (51.7%)* |
| Dose of Compound (I-6) (inhibitory rate) | 0.02 | μg/kg | (3.4%) | 0.065 | μg/kg | (43.1%) |
|  | 0.13 | μg/kg | (52.9%)* | 0.65 | μg/kg | (35.6%) |

The numerical values with parenthesis in the Table express the inhibitory rate of the ulcer index of the group administered with the test drug to the ulcer index of the control group. The test drugs (compounds of the present invention) were all administered in the stomach through an oral catheter. * indicates $p < 0.05$.

TOXICITY

In acute toxicity test of the compound (I-1) through (I-6) of the present invention using ddY strain male mice, death of the animal did not occur, even with the does of 1 mg/kg, corresponding to approximately 1,000 to 100,000 times the effective dose on the animal through intravenous administration.

DOSE AND MODE OF ADMINISTRATION

The therapeutic and prophylactic agents for peptic ulcers comprising the compound (I) of the present invention are effective as treating and preventive drugs against ulcers of mammals (human, horse, dog, mouse, rat and the like).

The therapeutic and prophylactic agents for peptic ulcers of the present invention can be administered orally or parenterally. In the case of oral administration, the compound (I) is appropriately mixed with pharmaceutically acceptable additives (carriers, excipients, diluents, or the like), which are used as powders, tablets, capsules, troaches, mixtures, syrups or granules. In the case of parenteral administration, aqueous solutions or non-aqueous suspensions can be used as injections such as intravenous injection, intramuscular injection, subcutaneous injection or the like or suppositories, etc., containing the active drug can be used.

Dose may vary depending upon condition, body weight, age and the like of the patient but a daily dose of 0,1 to 1,5 mg calculated as the compound (I) is generally preferred for an adult, which is administered in one daily dose or divided into several doses, say 3 or 4 doses per diem.

The therapeutic and prophylactic agents for peptic ulcers comprising the compound (I) exhibit extremely effective therapeutic and prophylactic activity on peptic ulcers, with extremely low toxicity. Further, the pharmacological effect is remarkable and the compositions are extremely useful as therapeutic and prophylactic drugs for ulcers.

The present invention will be described in more detail with reference to the examples below but is not deemed to be limited thereto.

EXAMPLE 1

TABLET

The following components are used to prepare the tablets according to the present invention.

| (1) | Compound (I-1) | 0.5 mg |
| --- | --- | --- |
| (2) | Fine Grain No. 209 for direct tableting (manufactured by Fuji Chemical Industry Co., Ltd.) | 46.6 mg |
|  | Magnesium metasilicate alminate | 20 wt % |
|  | Corn Starch | 30 wt % |
|  | Lactose | 50 wt % |
| (3) | Crystalline cellulose | 24.0 mg |
| (4) | CMC calcium | 4.0 mg |
| (5) | Magnesium stearate | 0.4 mg |

(1), (3) and (4) were all previously passed through a sieve of 100 mesh. These (1), (3) and (4) were dried, respectively, to reduce the moisture content to a definite ratio. Thereafter, they were mixed in the weight ratios described above using a mixer. (5) was added to the homogeneously mixed powders followed by mixing for a short time (30 seconds). The powder mixture was tableted (pestle, 6.3 mm$\phi$, 6.0 mmR) to give tablets each weighing 75.5 mg.

Tablets containing the compounds (I-2), (I-3), (I-4), (I-5) and (I-6), respectively, instead of the compound (I-1) were prepared in the same manner as described above.

The tablets may also be coated, if necessary and desired, with a gastric film coating agent (e.g., polyvinylacetal diethylaminoacetate) or with an edible coloring agent, conventionally used.

EXAMPLE 2

| Capsule | | |
| --- | --- | --- |
| (1) | Compound (I-1) | 2.5 mg |
| (2) | Lactose | 935 mg |
| (3) | Magnesium stearate | 15 mg |

The compounds described above were weighed and then homogeneously mixed. The powder mixture was packed in hard gelatin capsules by 190 mg each.

Capsules containing the compounds (I-2), (I-3), (I-4), (I-5) and (I-6), respectively, instead of the compound (I-1) were prepared in the same manner as described above.

EXAMPLE 3

| Injection | | |
| --- | --- | --- |
| (1) | Compound (I-1) | 0.5 mg |
| (2) | Glucose | 100 mg |
| (3) | Physiological saline | 10 ml |

After filtering the solution mixture described above through a membrane filter, the mixture was again subjected to sterile filtration. The filtarate was aseptically divided into vials. After filling with nitrogen gas, the vials were sealed to prepare injections for intravenous administration.

Injections containing the compounds (I-2), (I-3), (I-4), (I-5) and (I-6), respectively, instead of the compound (I-1) were prepared in the same manner as described above.

While the invention has been described in detail and with reference to specific embodiments thereof, it will be apparent to one skilled in the art that various changes and modifications can be made therein without departing from the spirit and scope thereof.

What is claimed is:

1. A unit dosage therapeutic and/or prophylactic agent for peptic ulcers comprising in an amount effective to therapeutically and/or prophylactically treat peptic ulcer, a cyclohexane derivative represented by formula (I):

$$\begin{matrix} R^5 & R^4 \\ & A \\ R^6 & \\ & R^1 \\ & R^2 \end{matrix} \quad (I)$$

wherein A represents a group shown by formula, $>CH_2$, $$\begin{matrix} R^7 \\ | \\ C-X- \\ / \end{matrix} \begin{matrix} Y \\ \diagdown \\ R^3 \end{matrix} \text{ or } \begin{matrix} \diagdown \\ / \end{matrix} C=C=CH- \begin{matrix} Y \\ \diagdown \\ R^3 \end{matrix},$$

wherein X represents ethynylene, vinylene or ethylene, Y represents oxo or a hydroxy group; $R^1$, $R^4$ and $R^5$ each represents an alkyl group; $R^2$ represents a hydrogen atom or a group shown by —$OR^8$; $R^3$ represents a hydrogen atom or an alkyl group;

$R^6$ represents a hydrogen atom, oxo or a group shown by —$OR^8$; and $R^7$ represents a hydrogen atom or a group shown by —$OR^8$, wherein $R^8$ represents a hydrogen atom or an organic residue, and a pharmaceutically acceptable carrier.

2. The therapeutic and/or prophylactic agent of claim 1, wherein the alkyl group has from 1 to 6 carbon atoms.

3. The therapeutic and/or prophylactic agent of claim 2, wherein the alkyl group has from 1 to 4 carbon atoms.

4. The therapeutic and/or prophylactic agent of claim 1, wherein the organic residue is alkyl, acyl, alkoxycarbonyl, alkoxycarbonylalkyl, carboxyalkyl, carboxyalkylcarbonyl, cyclic acetal or an oligosaccharide residue having from 1 to 3 sugar units.

5. A method for treating peptic ulcers in a mammal which comprises administering to the mammal a therapeutically and/or prophylactically effective amount of a cyclohexane derivative represented by general formula (I):

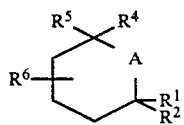

wherein A represents a group shown by formula, $>CH_2$,

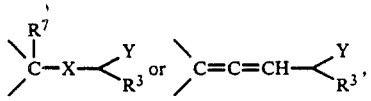

wherein X represents ethynylene, vinylene or ethylene, Y represents oxo or a hydroxy group; $R^1$, $R^4$ and $R^5$ each represents an alkyl group; $R^2$ represents a hydrogen atom or a group shown by $-OR^8$; $R^3$ represents a hydrogen atom or an alkyl group;

$R^6$ represents a hydrogen atom, oxo or a group shown by $-OR^8$; and $R^7$ represents a hydrogen atom or a group shown by $-OR^8$, wherein $R^8$ represents a hydrogen atom or an organic residue.

6. The method for treating peptic ulcers of claim 5, wherien the alkyl group has from 1 to 6 carbon atoms.

7. The method for treating peptic ulcers of claim 6, wherein the alkyl group has from 1 to 4 carbon atoms.

8. The method for treating peptic ulcers of claim 5, wherein the organic residue is alkyl, acyl, alkoxycarbonyl, alkoxycarbonylalkyl, carboxyalkyl, carboxyalkylcarbonyl, cyclic acetal or an oligosaccharide residue having from 1 to 3 sugar units.

* * * * *